(12) United States Patent
Donovan et al.

(10) Patent No.: US 7,473,242 B2
(45) Date of Patent: Jan. 6, 2009

(54) METHOD AND SYSTEMS FOR TREATING VULNERABLE PLAQUE

(75) Inventors: Maura G. Donovan, St. Paul, MN (US); Alexander J. Karnauskas, Chicago, IL (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 727 days.

(21) Appl. No.: 10/834,711

(22) Filed: Apr. 29, 2004

(65) Prior Publication Data
US 2004/0220607 A1 Nov. 4, 2004

Related U.S. Application Data

(60) Provisional application No. 60/467,007, filed on Apr. 30, 2003.

(51) Int. Cl.
*A61M 29/00* (2006.01)
(52) U.S. Cl. .................................. 604/103.01
(58) Field of Classification Search ............ 604/103.01, 604/103.02, 103.08
See application file for complete search history.

(56) References Cited

U.S. PATENT DOCUMENTS

| 4,873,978 | A |   | 10/1989 | Ginsburg |
|---|---|---|---|---|
| 4,950,232 | A | * | 8/1990 | Ruzicka et al. ............... 604/43 |
| 5,011,488 | A |   | 4/1991 | Ginsburg |
| 5,100,429 | A | * | 3/1992 | Sinofsky et al. ............ 623/1.21 |
| 5,545,132 | A | * | 8/1996 | Fagan et al. ............ 604/103.08 |
| 5,611,775 | A | * | 3/1997 | Machold et al. ............. 604/509 |
| 6,048,332 | A | * | 4/2000 | Duffy et al. ............ 604/103.08 |
| 6,190,358 | B1 |   | 2/2001 | Fitzmaurice et al. |
| 6,245,026 | B1 |   | 6/2001 | Campbell et al. |
| 6,346,116 | B1 |   | 2/2002 | Brooks et al. |
| 6,398,773 | B1 |   | 6/2002 | Bagaoisan et al. |
| 6,500,147 | B2 |   | 12/2002 | Omaleki et al. |
| 7,048,717 | B1 | * | 5/2006 | Frassica ................ 604/165.04 |

* cited by examiner

*Primary Examiner*—Kevin T Truong

(57) ABSTRACT

Method and systems for treating a vulnerable plaque associated with a blood vessel of a patient are disclosed. The method includes positioning an endoluminal device within a lumen of the blood vessel. An expandable member of the endoluminal device is expanded adjacent a wall of the blood vessel. A blood vessel coating substance is administered from the expanded expandable member. The administered blood vessel coating substance adheres to the wall of the blood vessel. A first system includes an endoluminal device including at least one aperture formed therein. An expandable member is operably attached to the endoluminal device. The expandable member comprises an outer surface including at least one groove disposed thereon. The expandable member is expanded within the blood vessel and a blood vessel coating substance is administered through the aperture and onto the expandable member outer surface. A second system includes means for positioning an endoluminal device within a lumen of the blood vessel and means for expanding an expandable member of the endoluminal device adjacent a wall of the blood vessel. The second system further includes means for administering a blood vessel coating substance from the expanded expandable member and means for adhering the administered blood vessel coating substance to the wall of the blood vessel.

21 Claims, 4 Drawing Sheets

METHOD AND SYSTEMS FOR TREATING VULNERABLE PLAQUE

RELATED APPLICATION

This application claims priority to U.S. Provisional Application No. 60/467,007, "Method and System for Treating Vulnerable Plaque" to Maura G. Donovan, filed Apr. 30, 2003, the entirety of which is incorporated by reference.

TECHNICAL FIELD OF THE INVENTION

The present invention relates generally to the field of vascular therapies. More particularly, the invention relates to strategies for treating a vulnerable plaque associated with a blood vessel of a patient.

BACKGROUND OF THE INVENTION

Heart disease, specifically coronary artery disease (CAD), is a major cause of death, disability, and healthcare expense. Until recently, most heart disease was considered to be primarily the result of a progressive increase of hard plaque in the coronary arteries. This atherosclerotic disease process of hard plaques leads to a critical narrowing (stenosis) of the affected coronary artery and produces anginal syndromes, known commonly as chest pain. The progression of the narrowing reduces blood flow, triggering the formation of a blood clot. The clot may choke off the flow of oxygen rich blood (ischemia) to heart muscles, causing a heart attack. Alternatively, the clot may break off and lodge in another organ vessel such as the brain resulting in a thrombotic stroke.

Within the past decade, evidence has emerged expanding the paradigm of atherosclerosis, coronary artery disease, and heart attacks. While the build up of hard plaque may produce angina and severe ischemia in the coronary arteries, new clinical data now suggests that the rupture of sometimes non-occlusive, vulnerable plaques causes the vast majority of heart attacks. The rate is estimated as high as 60-80 percent. In many instances vulnerable plaques do not impinge on the vessel lumen, rather, much like an abscess they are ingrained under the arterial wall. For this reason, conventional angiography or fluoroscopy techniques are unlikely to detect the vulnerable plaque. Due to the difficulty associated with their detection and because angina is not typically produced, vulnerable plaques may be more dangerous than other plaques that cause pain.

Atherosclerotic plaques vulnerable to rupture are typically small deposits covered by thin fibrous caps (less than 70 microns) covering lipid cores. Within the fibrous cap is a dense infiltrate of smooth muscle cells, macrophages and lymphocytes. The lipid pool is believed to be formed as a result of a pathological process involving low density lipoprotein (LDL), macrophages, and the inflammatory process. The macrophages oxidize the LDL producing foam cells. The macrophages, foam cells, and smooth muscle cells sit beneath the endothelium and release various toxic substances, such as tumor necrosis factor and tissue factor. These substances damage the arterial wall and surrounding areas and can result in generalized cell necrosis and apoptosis, pro-coagulation, and weakening of the fibrous cap. The inflammation process may weaken the fibrous cap to the extent that sufficient mechanical stress, such as that produced by increased blood pressure, may result in rupture. The lipid core and other contents of the vulnerable plaque (emboli) may then spill into the blood stream thereby initiating a clotting cascade. The cascade produces a blood clot (thrombosis) that potentially results in a heart attack and/or stroke. The process is exacerbated due to the release of collagen and other plaque components (e.g., tissue factor), which enhance clotting upon their release.

Several strategies have been developed for the detection (e.g., diagnosis and localization) of vulnerable plaques. One strategy involves the measurement of temperature within a blood vessel. For example, vulnerable plaque tissue temperature is generally elevated compared to healthy vascular tissue. Measurement of this temperature discrepancy may allow detection of the vulnerable plaque.

Another detection strategy involves labeling vulnerable plaque with a marker. The marker substance may be specific for a component and/or characteristic of the vulnerable plaque. For example, the marker may have an affinity for the vulnerable plaque, more so than for healthy tissue. Detection of the marker may thus allow detection of the vulnerable plaque. Alternatively, the marker may not necessarily have an affinity for the vulnerable plaque, but will simply change properties while associated with the vulnerable plaque. The property change may be detected and thus allow detection of the vulnerable plaque.

Regardless of the strategy used for detection, a formidable problem remains in the treatment of the vulnerable plaque. Without appropriate treatment, the vulnerable plaque may rupture and subsequently release embolic material and cause great risk to the patient. Drug and other therapies exist that may reduce the size and chance of vulnerable plaque rupture over a relatively long time frame. These therapies, however, may not be desirable or effective for all patients, including those having vulnerable plaques on the immediate verge of rupture. With such therapies, accidental or unanticipated rupture of these truly vulnerable plaques may occur in a non-clinical setting. Therefore, it would be desirable to provide a treatment strategy that would prevent or at least minimize the deleterious sequelae associated with vulnerable plaque rupture. Furthermore, it would be desirable for such a treatment strategy to prevent any potential embolic material from escaping a ruptured vulnerable plaque and causing risk to the patient.

Accordingly, it would be desirable to provide a strategy for treating vulnerable plaque that would overcome the aforementioned and other disadvantages.

SUMMARY OF THE INVENTION

A first aspect according to the invention provides a method of treating a vulnerable plaque associated with a blood vessel of a patient. The method includes positioning an endoluminal device within a lumen of the blood vessel. An expandable member of the endoluminal device is expanded adjacent a wall of the blood vessel. A blood vessel coating substance is administered from the expanded expandable member. The administered blood vessel coating substance adheres to the wall of the blood vessel.

A second aspect according to the invention provides a system for treating a vulnerable plaque associated with a blood vessel of a patient. The system includes an endoluminal device including at least one aperture formed therein. An expandable member is operably attached to the endoluminal device. The expandable member comprises an outer surface including at least one groove disposed thereon. The expandable member is expanded within the blood vessel and a blood vessel coating substance is administered through the aperture and onto the expandable member outer surface.

A third aspect according to the invention provides a system for treating a vulnerable plaque associated with a blood vessel of a patient. The system includes means for positioning an endoluminal device within a lumen of the blood vessel and means for expanding an expandable member of the endoluminal device adjacent a wall of the blood vessel. The second system further includes means for administering a blood vessel coating substance from the expanded expandable member and means for adhering the administered blood vessel coating substance to the wall of the blood vessel.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DESCRIPTION OF THE PRESENTLY PREFERRED EMBODIMENTS

Figure 1:
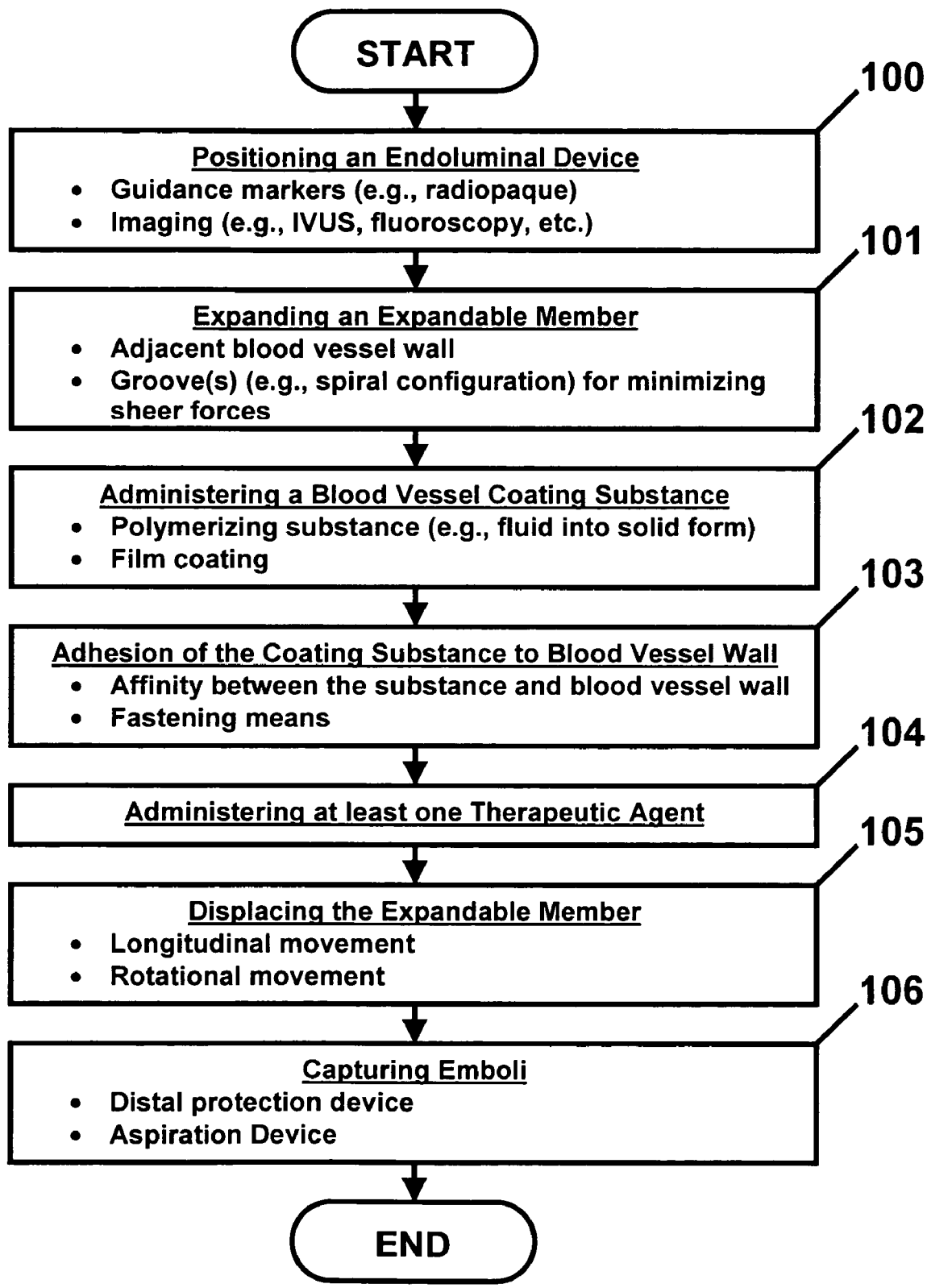
FIG. 1 is a flow chart of a method of treating a vulnerable plaque associated with a blood vessel of a patient, in accordance with the present invention.

Referring to the drawings, wherein like reference numerals refer to like elements, FIG. 1 is a flow chart of a method of treating a vulnerable plaque associated with a blood vessel of a patient, in accordance with one embodiment of the present invention. A vulnerable plaque is distinguishable from other types of plaque, including hard plaques, by the presence of a fibrous cap. The vulnerable plaque fibrous cap retains a pool of lipids and other contents, which may be released into the blood vessel upon rupture. The released contents may form emboli that can lodge in a blood vessel thereby posing a risk to the patient. Vulnerable plaques, unlike hard plaques, are generally non-occlusive and as such, may not produce angina. The following description pertains to treatment of these vulnerable plaques.

Those skilled in the art will recognize that although the present invention is described primarily in the context of treating a vulnerable plaque while using specific pharmacological agents, the inventors contemplate a broader method of application. Any number of treatment systems and devices capable of performing the prescribed function(s) may be compatible with the present invention. Furthermore, the treatment of the vulnerable plaque is not limited to the described strategies. Numerous modifications, substitutions, and variations may be made to the method and systems while providing effective vulnerable plaque treatment consistent with the present invention.

In the following description, vulnerable plaque treatment is described in the context of a catheterization procedure for a human patient. The vulnerable plaque may be treated in a clinical setting thereby allowing for controlled treatment in an environment in which immediate care is given. Treating the vulnerable plaque in a manner according to the present invention may prevent the accidental or unanticipated release of emboli in a non-clinical setting. As such, complications stemming from vulnerable plaque rupture, such as heart attack and stroke, may be avoided. It should be noted that the term "detect" and derivatives thereof, when used in regard to vulnerable plaque, refer to the diagnosis and, optionally, the localization of the lesion.

As shown in FIG. 1, vulnerable plaque treatment may begin by positioning an endoluminal device within a lumen of the blood vessel (step 100).

Figure 2:
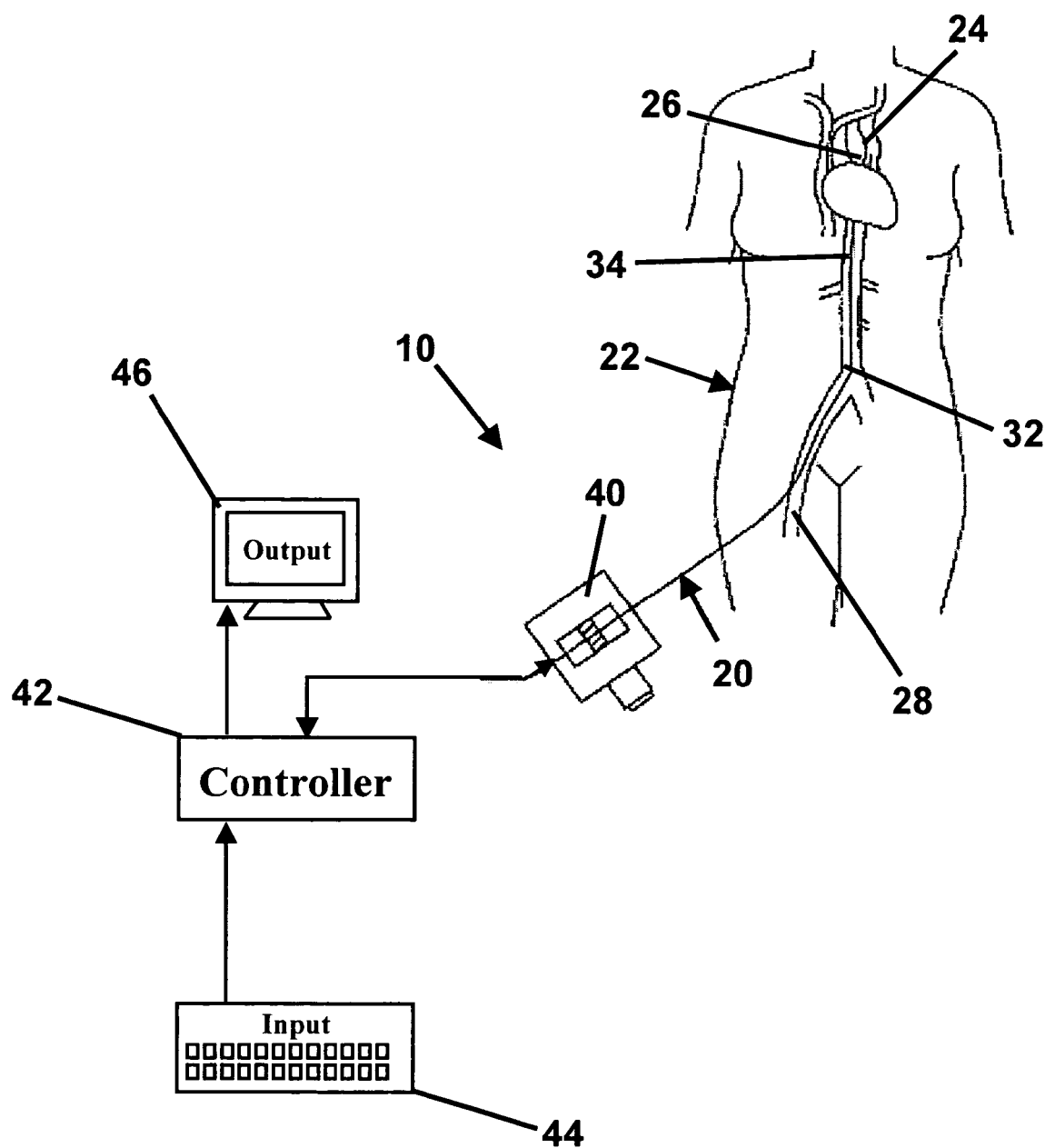
FIG. 2 is a schematic view of a vulnerable plaque detection procedure within a patient, in accordance with the present invention.

Referring to FIG. 2, a system 10 for treating a vulnerable plaque, shown generally by numeral 10, includes the endoluminal device 20, which may be positioned within a patient 22 at a predetermined vascular treatment site 24 designated for vulnerable plaque treatment. Patient 22 treatment site 24, which in this case is in an aortic vessel 26, may be accessed through various blood vessels. In one embodiment, the treatment site 24 may be accessed percutaneously through an incision made in patient 22 femoral artery 28. In another embodiment, another vessel such as a subclavian artery may be used to access the treatment site. Endoluminal device 20 may be advanced to the treatment site 24 through a vessel pathway, which in this case includes an iliac artery 32 and abdominal aorta 34. It is important to note that pathways and treatment site other than the ones illustrated and described may be used with the present invention. In addition, the described methodology order may be varied to achieve vulnerable plaque detection and treatment.

The treatment site 24 may be predetermined as a result of a vulnerable plaque diagnostic procedure. Numerous such detection procedures are known in the art and may be adapted for use with the present invention. The strategies include, but are not limited to, temperature detection strategies, labeling strategies, imaging strategies, general strategies for discriminating the vulnerable plaque from surround healthy vascular tissue, and the like.

The temperature detection strategies may include a comparison of the temperature of various portions of a blood vessel. The temperature of the vulnerable plaque is typically one or more degrees Celsius higher than healthy vascular tissue because of increased metabolic activity (i.e., inflammation). For example, a relatively normal blood vessel temperature may be about 37° C. whereas the vulnerable plaque may have a localized temperature as high as 40° C. As such, the temperature sensing device may be used to detect vulnerable plaque(s). Numerous devices for sensing temperature are known in the art. By way of example, the temperature sensing device may be a thermography catheter analogous to that described in U.S. Pat. No. 6,245,026 to Campbell et al. As another example, a guidewire including thermal sensors and any number of other devices known in the art may be used for sensing vessel temperature and detecting the vulnerable plaque.

Other detection strategies may utilize any number of properties specific to a vulnerable plaque for detection. For example, vulnerable plaques generally include a localized concentration of specific lipids, proteins, and factors. Measurement of these components may facilitate detection. The detection may be achieved and/or enhanced by labeling. For example, the vulnerable plaque may be labeled with an antibody marker specific for a plaque component wherein the antibody may include a radiolabel. The radiolabel may then be detected with an appropriate detection device known in the art.

The vulnerable plaque may be detected endovascularly as with, for example, a catheter based platform. Alternatively, the vulnerable plaque may be detected from external the blood vessel. For example, a device for detecting the vulnerable plaque may be positioned through an incision in the patient. The device may then detect the vulnerable plaque without the need for catheterization. During such a procedure, detection may be achieved during open surgery or in a minimally invasive manner. As another example, the vulnerable plaque may be detected external to the patient, such as with an imaging device (e.g., devices utilizing magnetic resonance, ultrasound, infra-red, fluorescence, visible light, radio waves, x-ray, etc.). Those skilled in the art will recognize that the strategy for detecting the vulnerable plaque may vary from the described methods. Numerous methods and devices for the detection of vulnerable plaque may be adapted for use with the present invention.

The vulnerable plaque diagnostic procedure may be performed in a previous procedure distinct from treatment or, alternatively, as a common medical procedure. Furthermore, the diagnostic procedure need not detect the precise location of the vulnerable plaque(s). The treatment procedure of the present invention may be employed in vascular region(s) merely suspected of including vulnerable plaque (i.e., a prophylactic-type treatment). For example, a patient determined to have an elevated risk of vulnerable plaque may undergo a treatment strategy in accordance with the present invention at various region(s) generally known to include such plaques.

System 10 may further include a movement apparatus 40, such as a motorized pullback device, for providing controlled and precise positioning and movement of the endoluminal device 20 and/or its various components. Such movement apparatuses are known or may be constructed by those skilled in the art. A controller 42 may be operably coupled to the movement apparatus 40. Controller 42 may be, for example, a computerized central processing unit running a program for providing controlled and precise positioning and movements of the endoluminal device 20. The movements may include advance, retreat, and/or rotational movements.

An input device 44, such as a keyboard and/or mouse, may provide means for inputting information to the controller 42 by an operator (not shown). The operator may specify parameters of the vulnerable plaque diagnostic and/or treatment procedure(s) through the input device 44. For example, the operator may specify endoluminal device 20 positioning and movements, and delivery of substances and/or therapeutic agents associated with the present invention. The input device 44 may facilitate real-time control of the procedure.

An output device 46, such as a monitor, may be operably attached to the controller 42 for displaying information and status of the diagnostic procedure, the treatment procedure, the received input, the positioning and movements of the endoluminal device 20, and/or other information relevant to the medical procedure(s). The operator may monitor the progress of the medical procedure(s) through the output device 46. For example, the positioning of the endoluminal device 20 may be provided in real-time via the output device 46. Those skilled in the art will recognize that imaging strategies (e.g., intravascular ultrasound (IVUS), fluoroscopy, etc.) may be utilized in conjunction with the presently described vulnerable plaque treatment strategy to facilitate the proper positioning of the endoluminal device 20 within the patient 22.

Once the endoluminal device is properly positioned, an expandable member of the endoluminal device is expanded adjacent a wall of the blood vessel (step 101).

Figure 3:
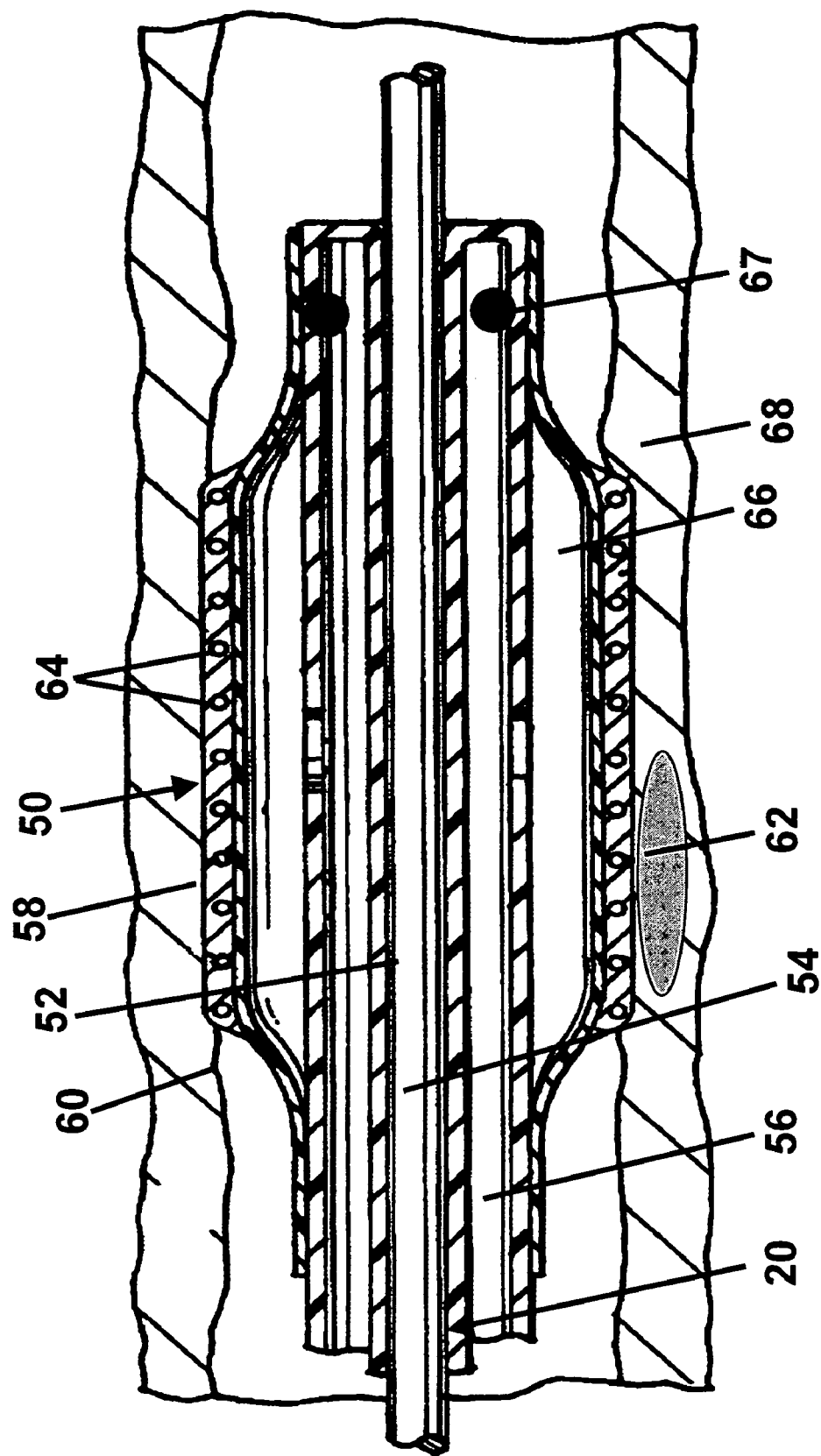
FIG. 3 is a partial cross-sectional view of an expandable member disposed on the endoluminal device, in accordance with the present invention.

Referring to FIG. 3, a partial cross-sectional view of an expandable member 50 disposed on the endoluminal device 20 is shown. Endoluminal device 20 may be any number of devices for carrying an expandable member 50 thereon. In one embodiment, the endoluminal device 20 may be a flexible catheter including a first lumen 52 formed therein for carrying a guide wire 54 in an over-the-wire configuration as known in the art. Endoluminal device 20 may further include a second lumen 56, and optionally additional lumen(s), formed therein in for providing delivery of a blood vessel coating substance and one or more therapeutic agents.

In one embodiment, the expandable member 50 may be any number of devices adapted to radially expand from a collapsed configuration. For example, the expandable member 50 may be a balloon manufactured from a resilient material. Expandable member 50 is shown in a fully expanded configuration wherein one or more outer surfaces 58 are positioned adjacent a vessel wall 60. Preferably, the expandable member 50 is not sufficiently expanded so as to exert sufficient forces onto the vessel wall 60, which may potentially lead to vulnerable plaque 62 rupture. Expandable member 50 may further include a plurality of apertures 64 formed within the outer surfaces 58 for allowing delivery of the blood vessel coating substance and therapeutic agent(s) from an inner lumen 66.

Expandable member 50 may be advanced through a patient's blood vessel network in the collapsed configuration. At least one (radiopaque) marker 67 may be disposed on the endoluminal device 20 and/or expandable member 50 to allow in situ visualization and proper positioning. The marker(s) may be manufactured from a number of materials used for visualization in the art including radiopaque materials platinum, gold, tungsten, metal, metal alloy, and the like. Marker 67 may be visualized by fluoroscopy, IVUS, and other methods known in the art.

Once properly positioned, the expandable member 50 may be "inflated" to the fully expanded, or deployed, configuration shown to allow treatment of a vulnerable plaque 62 associated with a blood vessel 68. Upon completion of treatment, the expandable member may be "deflated" re-establishing the collapsed configuration thereby facilitating withdrawal of the endoluminal device 20 from the patient. Strategies for operably inflating and deflating an expandable member, such as a balloon, are well recognized in the art. In one example, a pressurized delivery and withdrawal of the blood vessel coating substance, therapeutic agent(s), and/or other fluids (e.g., gasses or liquids) into the inner lumen 66 may be used to achieve inflation and deflation of the expandable member 50.

Those skilled in the art will recognize the numerous endoluminal devices may be adapted for use with the present invention. A first suitable exemplary endoluminal device includes the flexible balloon catheter disclosed by U.S. Pat. No. 6,500,147 issued to Omaleki et al. on Dec. 31, 2002 and assigned to Medtronic PercuSurge, Inc. of Santa Rosa, Calif. (US). A second suitable example suitable exemplary endoluminal device includes the reinforced rapid exchange catheter disclosed by U.S. Pat. No. 6,190,358 issued to Fitzmaurice et al. on Feb. 20, 2001 and assigned to Medtronic AVE, Inc. of Santa Rosa, Calif. (US).

After the expandable member is properly expanded, the blood vessel coating substance is administered (step 102).

Figure 4:
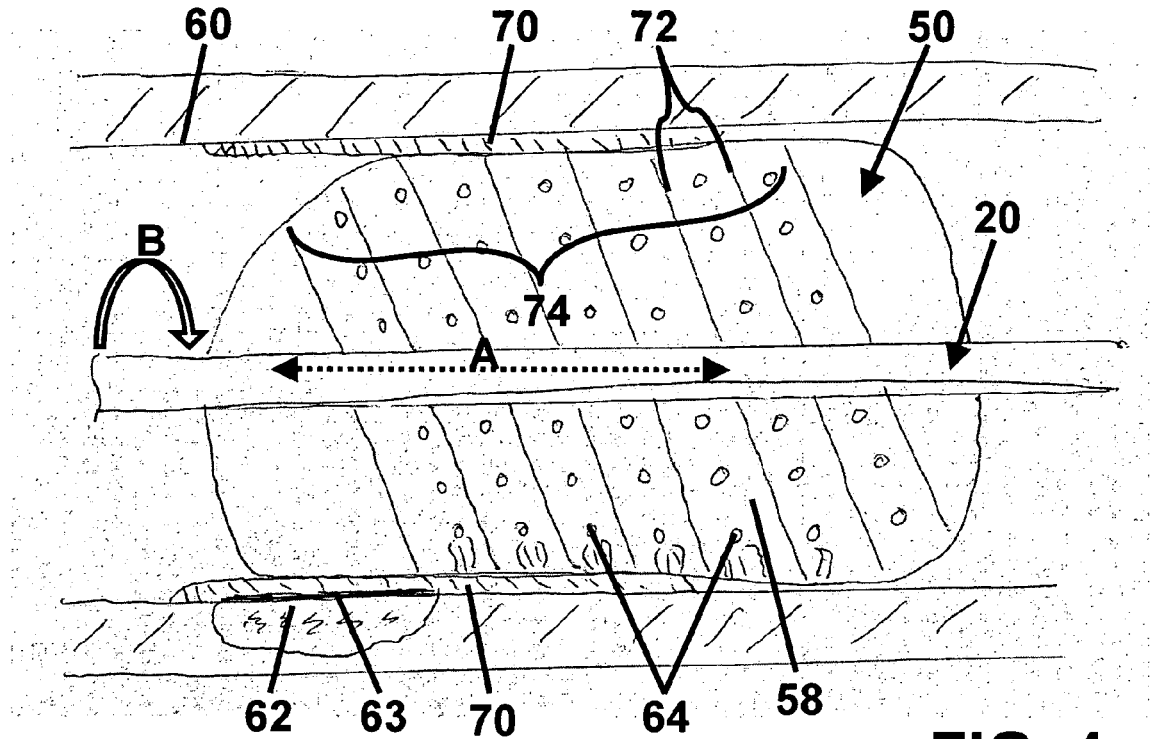
FIG. 4 is a partial cross-sectional view of a blood vessel coating substance administration through apertures form in an outer surface of an expandable member, in accordance with the present invention.

Referring to FIG. 4, the blood vessel coating substance 70 is administered through the apertures 64 and onto the outer surface 58 of the expandable member 50. In one embodiment, the coating substance 70 may be at least one substance such as cellulose, hydroxypropyl methyl cellulose, fibrinogen, thrombin, a glucose polymer, a polymer, a monomer, a cross-linking agent, a binding agent, a thickening agent, cellulose ether, an epoxy, a polyolefin, a polyethylene, a vinyl, a plastic, a polysaccharide, a biocompatible compound, a biodegradable compound, a heat sensitive compound, and Methocel™. Furthermore, the coating substance 70 may be a fluid that upon administration polymerizes into a solid or a semi-solid. The administered coating substance 70 preferably provides a reinforcing surface (e.g., a film coating) to strengthen or "shore-up" a relatively thin fibrous cap 63 of the vulnerable plaque 62 while offering relatively little frictional resistance to the vessel blood flow.

In a first working example, the coating substance 70 may be a heat sensitive and biocompatible cellulose ether such as Methocel™ (sold by Dow Chemical Co.) is administered as a liquid and, upon exposure to a body temperature at about 37 degrees Celsius, forms a solid film coating. In a second working example, the coating substance 70 may include two or more component substances, such as an epoxy compound (e.g., a resin and cross-linker), a monomer and a cross-linker, fibrin and thrombin, and the like wherein one component substance effects polymerization of another components substance upon their combination. The ratio of the component substance may be predetermined as known in the art to provide optimal coating substance 70 consistency and other properties (i.e., increasing the concentration of a cross-linking agent relative to a monomer may provide a more durable coating substance 70 film and a shorter polymerization time).

In one embodiment, the expandable member 50 outer surface 58 may include at least one groove 72 disposed thereon. Groove 72 may be a ridged surface wherein the apertures 64 are positioned within ridge pits. Further, the groove 72 may be in a spiral configuration 74 positioned around a circumference of the expandable member 50. When administered through the apertures 64 positioned within the groove 72 (i.e., within the pits), the coating substance 70 may efficiently polymerize. The ridge pit geometry may minimize blood flow sheer forces (i.e., by "shielding") that can otherwise interfere with the polymerization process by carrying away or diluting the coating substance 70. Those skilled in the art will recognize that numerous outer surface and/or ridge geometries may be provided to effectively facilitate the administration of the blood vessel coating substance 70.

After administration, the blood vessel coating substance adheres on the wall of the blood vessel (step 103).

In one embodiment, the adherence of the vessel coating substance 70 comprises an affinity between the substance, the fibrous cap, and the vascular endothelia (e.g., electrostatic forces, London forces, dipole-dipole forces, hydrogen bonding, and the like). The coating substance 70 may include various molecular subgroups, modifications, and moieties as known in the art for providing or enhancing the affinity. Preferably, the administered coating substance 70 (e.g., the film coating) remains associated with the vessel at the site of administration. The affinity provides a strategy for retaining the administered coating substance 70 to the vessel wall 60 thereby preventing it from displacement due to the sheer forces of the blood stream and/or movement of the vessel.

In another or the same embodiment, the adherence of the vessel coating substance comprises one or more fastening means (not shown) for retaining the administered coating substance to the vessel wall. For example, a variety or fasteners, clips, and the like may be used. Those skilled in the art will recognize that a wide variety of strategies may be used for achieve retention of the administered coating substance 70 in accordance with the present invention.

During the treatment procedure, at least one therapeutic agent may be administered (step 104).

In one embodiment, the therapeutic agent(s), which typically provide a treatment benefit, may be administered at a various time points of the treatment procedure. Furthermore, the agent(s) may be administered via numerous strategies such as intravenous administration, catheter administration, infusion of the therapeutic agent with the vessel coating substance 70, and the like. The treatment benefits of the therapeutic agent may include contribution to vulnerable plaque healing, reduction in vulnerable plaque size, change in vulnerable plaque constitution, prevention or minimization of vulnerable plaque rupture risk, strengthening of the fibrous cap, beneficial cardiac effects, prevention or minimization of clot formation, and the like.

Suitable therapeutic agents that may be used with embodiments according to the invention include, but are not limited to angiogenic agents, antiarteriosclerotic agents, antiarythmic agents, antibiotics, antidiabetic afents, antiendothelin agents, antiinflammatory agents, antimitogenic factors, antioxidants, antiplatelet agents, antiproliferative agents, antisense agents, antisense agents, antithrombogenic agents, calcium channel blockers, clot dissolving enzymes, growth factor inhibitors, growth factors, immunosuppressants, nitrates, nitric oxide releasing agents, vasodilators, virus-mediated gene transfer agents, agents having a desirable therapeutic application, combinations of the above, and the like. Specific example of therapeutic agents include abciximab, angiopeptin, colchicine, eptifibatide, heparin, hirudin, lovastatin, methotrexate, streptokinase, Taxol®, ticlopidine, tissue plasminogen activator, trapidil, urokinase, and growth factors VEGF,TGF-beta, IGF, PDGF, and FGF.

The expandable member may then be optionally displaced relative to the blood vessel (step 105).

Referring again to FIG. 4, the movement apparatus may provide the displacement of the endoluminal device 20 and the expandable member 50. The displacement may include longitudinal movement along axis A and rotational movement around the axis, as shown by arrow B. In one embodiment, an elongated region of vessel wall 60 may be coated by moving the expandable member 50 in one direction along axis A with concurrent rotational movement B in one direction. This compound motion coupled with the groove 72 spiral configuration provides substantially a corkscrew-type motion. Coating substance 70 may be continually administered during the corkscrew-type motion thereby allowing addition to and elongation of the administered coating substance 70. In this manner, an elongated region of the vessel wall 60 may be coated.

During the treatment procedure, protective measures may be undertaken to protect from rupture of any vulnerable plaque (step 106).

Figure 5:
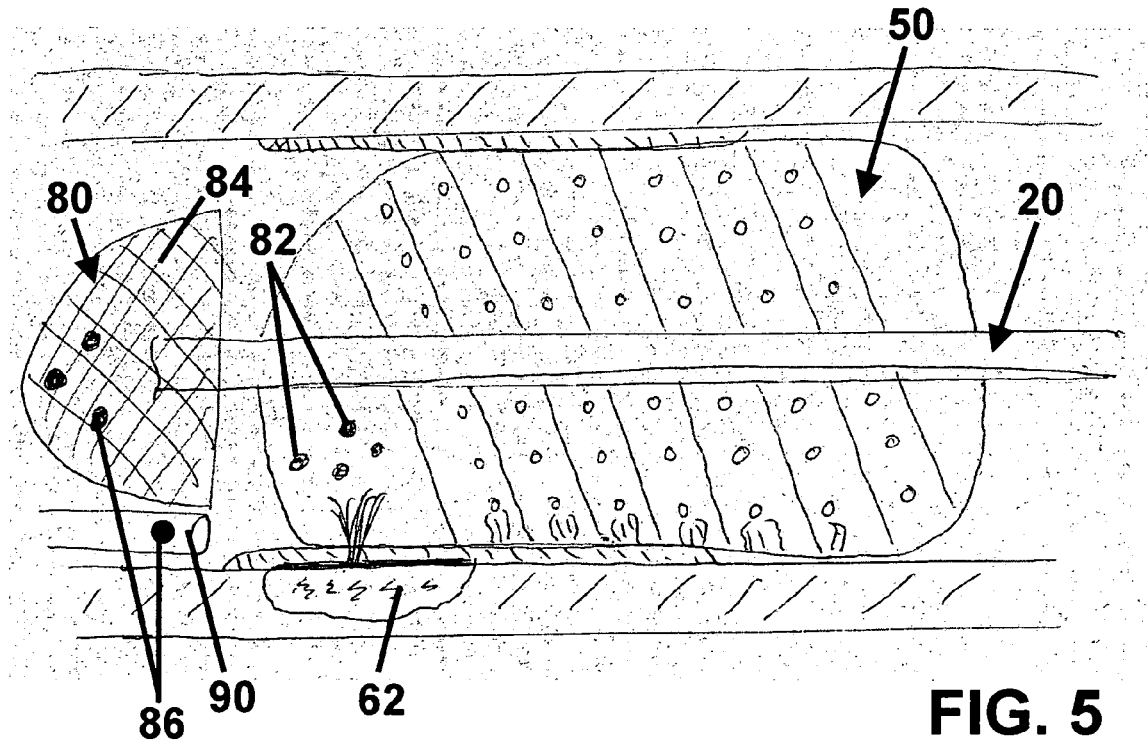
FIG. 5 is a partial cross-sectional view of a distal protection device deployed during a vulnerable plaque treatment procedure to prevent escape of potential embolic material, in accordance with the present invention.

In one embodiment as shown in FIG. 5, a distal protection device 80 may be deployed during the treatment procedure to prevent escape of potential embolic material 82. Distal protection device 80 may capture the embolic material 82 as they are carried by the flow of blood from an inadvertently ruptured vulnerable plaque. Distal protection device 80 may include a mesh filter 84 for trapping the embolic material 82 during the treatment procedure. The filter 84 may be then retracted to retain any captured emboli 86 and removed from the patient. Numerous distal protection devices for capturing emboli and methods of deployment are known in the art. By way of example, the distal protection device 80 may be a distal protection device analogous to that described in U.S.

Pat. No. 4,873,978 issued to Ginsburg on Oct. 17, 198 or U.S. Pat. No. 6,346,116 issued to Brooks et al. on Feb. 12, 2002 and assigned to Medtronic AVE, Inc. of Santa Rosa, Calif. (US). As another example, the distal protection device 80 may be a distal protection device analogous to the GuardWire Plus™ by Medtronic AVE, Inc.

In another or the same embodiment, the embolic material may be captured with an aspiration device 90. The aspiration device 90 may provide negative pressure thereby drawing embolic material 82 through the device 90 and may be positioned either upstream or downstream of the vulnerable plaque 62. Numerous aspiration devices for capturing emboli are known in the art. By way of example, the aspiration device 90 may be analogous to that described in U.S. Pat. No. 5,011,488 issued to Ginsburg on Apr. 30, 1991 or U.S. Pat. No. 6,398,773 issued to Bagaoisan et al. on Jun. 4, 2002 and assigned to Medtronic PercuSurge, Inc. As another example, the aspiration device 90 may be a device analogous to the Export™ Catheter by Medtronic AVE, Inc.

While the embodiments of the invention disclosed herein are presently considered to be preferred, various changes and modifications may be made without departing from the spirit and-scope of the invention. The systems, devices, and methods of utilizing the same are not limited to any particular design or sequence. Specifically, numerous endoluminal devices, expandable members, vessel coating substances, movement apparatuses, and capturing apparatuses may be adapted to achieve a vulnerable plaque treatment strategy in accordance with the present invention. The functions ascribed to the aforementioned devices, members, and apparatuses may be achieved with a single or with multiple devices, members, and apparatuses. Furthermore, the procedure step order and methods of achieving the same may vary without limiting the utility of the invention. For example, the location and length of blood vessel coating may vary to provide effective vulnerable plaque treatment.

Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

The invention claimed is:

1. A method of treating a vulnerable plaque associated with a blood vessel of a patient, the system comprising:
   positioning an endoluminal device within a lumen of the blood vessel;
   expanding an expandable member of the endoluminal device adjacent a wall of the blood vessel;
   administering a blood vessel coating substance from the expanded expandable member;
   displacing the expandable member relative to the blood vessel while administering the blood vessel coating substance;
   polymerizing the administered blood vessel coating substance; and
   adhering the polymerized administered blood vessel coating substance to the wall of the blood vessel.

2. The method of claim 1 wherein the blood vessel coating substance comprises at least one substance selected from a group consisting of methyl cellulose, hydroxypropyl methyl cellulose, fibrinogen, thrombin, a glucose polymer, a polymer, a monomer, a cross-linking agent, a binding agent, a thickening agent, cellulose ether, an epoxy, a polyolefin, a polyethylene, a vinyl, a plastic, a polysaccharide, a biocompatible compound, a biodegradable compound, a heat sensitive compound, and Methocel™.

3. The system of claim 1 wherein the administered blood vessel coating substance comprises a film coating.

4. The method of claim 1 further comprising minimizing blood flow sheer forces exerted on the administered blood vessel coating substance.

5. The method of claim 1 further comprising administering at least one therapeutic agent to the patient wherein said agent provides a treatment benefit.

6. The method of claim 1 further comprising capturing one or more emboli carried within the blood vessel.

7. The method of claim 1 wherein displacing the expandable member relative to the blood vessel while administering the blood vessel coating substance comprises longitudinally translating the expandable member.

8. The method of claim 1 wherein displacing the expandable member relative to the blood vessel while administering the blood vessel coating substance comprises rotating the expandable member.

9. A system for treating a vulnerable plaque associated with a blood vessel of a patient, the system comprising:
   an endoluminal device including at least one aperture formed therein;
   an expandable member operably attached to the endoluminal device, the expandable member comprising an outer surface including at least one groove disposed thereon;
   wherein the expandable member is expanded within the blood vessel;
   a movement apparatus operably connected to the expandable member and adapted for displacing the expandable member relative to the blood vessel; and
   a blood vessel coating substance, wherein the blood vessel coating substance is administered to the blood vessel through the aperture and onto the expandable member outer surface during displacement of the expandable member and wherein the blood vessel coating substance comprises a fluid that upon administration polymerizes into a solid or a semi-solid.

10. The system of claim 9 wherein the groove comprises a spiral configuration positioned around a circumference of the expandable member.

11. The system of claim 9 wherein the groove is adapted to minimize blood flow sheer forces exerted on the administered blood vessel coating substance.

12. The system of claim 9 wherein the blood vessel coating substance comprises at least one substance selected from a group consisting of methyl cellulose, hydroxypropyl methyl cellulose, fibrinogen, thrombin, a glucose polymer, a polymer, a monomer, a cross-linking agent, a binding agent, a thickening agent, cellulose ether, an epoxy, a polyolefin, a polyethylene, a vinyl, a plastic, a polysaccharide, a biocompatible compound, a biodegradable compound, a heat sensitive compound, and Methocel™.

13. The system of claim 9 wherein the blood vessel coating substance adheres to a wall of the blood vessel.

14. The system of claim 9 wherein the administered blood vessel coating substance comprises a film coating.

15. The system of claim 9 further comprising at least one therapeutic agent adapted for administration to the patient wherein said agent provides a treatment benefit.

16. The system of claim 9 further comprising a capturing apparatus operably attached to the device adapted to capture one or more emboli carried within the blood vessel.

17. The system of claim 9 wherein the movement apparatus is configured to rotate about a central axis and longitudinally translate to displace the expandable member relative to the blood vessel.

18. A system for treating a vulnerable plaque associated with a blood vessel of a patient, the system comprising:

means for positioning an endoluminal device within a lumen of the blood vessel;

means for expanding an expandable member of the endoluminal device adjacent a wall of the blood vessel;

means for administering a blood vessel coating substance from the expanded expandable member;

means for displacing the expanded expandable member relative to the blood vessel during administration of the blood vessel coating substance;

means for polymerizing the administered blood vessel coating substance; and means for adhering the administered blood vessel coating substance to the wall of the blood vessel.

19. The system of claim 18 further comprising means for minimizing blood flow sheer forces exerted on the administered blood vessel coating substance.

20. The system of claim 18 further comprising means for capturing one or more emboli carried within the blood vessel.

21. The system of claim 18 wherein the means for displacing the expandable member relative to the blood vessel during administration of the blood vessel coating substance is configured to rotate about a central axis and longitudinally translate to displace the expandable member relative to the blood vessel.

* * * * *